US011020355B2

(12) United States Patent
Rhodes et al.

(10) Patent No.: US 11,020,355 B2
(45) Date of Patent: Jun. 1, 2021

(54) METHOD OF ENCAPSULATING CANNABINOIDS IN PHOSPHOLIPID CARRIERS

(71) Applicant: NuVessl, Inc., Calgary (CA)

(72) Inventors: Tanya Rhodes, Largo, FL (US); Deborah Duffey, Safety Harbor, FL (US)

(73) Assignee: NuVessl, Inc., Calgary (CA)

( * ) Notice: Subject to any disclaimer, the term of this patent is extended or adjusted under 35 U.S.C. 154(b) by 0 days.

(21) Appl. No.: 16/560,470

(22) Filed: Sep. 4, 2019

(65) Prior Publication Data

US 2020/0078297 A1 Mar. 12, 2020

Related U.S. Application Data

(60) Provisional application No. 62/727,996, filed on Sep. 6, 2018.

(51) Int. Cl.
| | |
|---|---|
| *A61K 31/65* | (2006.01) |
| *A61K 31/353* | (2006.01) |
| *A61K 9/107* | (2006.01) |
| *A61K 47/24* | (2006.01) |
| *A61K 36/185* | (2006.01) |
| *A61K 9/70* | (2006.01) |
| *A61K 9/00* | (2006.01) |
| *A61K 9/06* | (2006.01) |
| *A61K 9/127* | (2006.01) |
| *A61K 31/05* | (2006.01) |
| *A61K 47/10* | (2017.01) |
| *A61K 9/51* | (2006.01) |
| *A61K 31/352* | (2006.01) |
| *A61K 47/44* | (2017.01) |

(52) U.S. Cl.
CPC ............ *A61K 9/7023* (2013.01); *A61K 9/006* (2013.01); *A61K 9/0014* (2013.01); *A61K 9/06* (2013.01); *A61K 9/1075* (2013.01); *A61K 9/127* (2013.01); *A61K 9/51* (2013.01); *A61K 31/05* (2013.01); *A61K 31/352* (2013.01); *A61K 31/353* (2013.01); *A61K 36/185* (2013.01); *A61K 47/10* (2013.01); *A61K 47/24* (2013.01); *A61K 47/44* (2013.01)

(58) Field of Classification Search
CPC ...... A61K 31/65; A61K 31/353; A61K 47/24; A61K 36/185
See application file for complete search history.

(56) References Cited

U.S. PATENT DOCUMENTS

| | | |
|---|---|---|
| 5,004,611 A | 4/1991 | Leigh |
| 5,009,819 A | 4/1991 | Popescu et al. |
| 5,269,979 A | 12/1993 | Fountain |
| 5,437,274 A | 8/1995 | Khoobehi et al. |
| 5,716,638 A | 2/1998 | Touitou |
| 5,814,343 A | 9/1998 | Jones et al. |
| 5,879,703 A | 3/1999 | Fountain |
| 5,885,921 A | 3/1999 | Krupey |
| 6,096,331 A | 8/2000 | Desai et al. |
| 6,203,778 B1 | 3/2001 | Brasch |
| 7,025,992 B2 | 4/2006 | Whittle |
| 8,545,874 B2 | 10/2013 | Fountain |
| 8,545,875 B2 | 10/2013 | Fountain |
| 8,597,678 B2 | 12/2013 | Fountain |
| 9,364,434 B2 | 6/2016 | Fountain |
| 9,399,015 B2 | 9/2016 | Fountain |
| 9,480,650 B2 | 11/2016 | Fountain |
| 9,635,876 B2 | 5/2017 | Fountain |
| 9,987,234 B2 | 6/2018 | Fountain |
| 10,240,115 B2 | 3/2019 | Fountain |
| 10,246,672 B2 | 4/2019 | Fountain |
| 10,266,800 B2 | 4/2019 | Fountain |
| 2001/0006643 A1 | 7/2001 | Hope |
| 2005/0191330 A1 | 9/2005 | Huglin |
| 2016/0030387 A1 | 2/2016 | Winnicki |
| 2016/0279073 A1 | 9/2016 | Donsky et al. |
| 2018/0296493 A1 | 10/2018 | Kaufman |

FOREIGN PATENT DOCUMENTS

WO     WO9916426     4/1999

OTHER PUBLICATIONS

Godin, B., et al., "Ethosomes: New prospects in Transdermal Delivery," Critical Reviews in Therapeutic Drug Carrier Systems, vol. 20(1), (2003) pp. 63-102.
Gruner, S. et al., "Novel Multilayered Lipid Vesicles: Comparison of Physical Characteristics of Multilamellar Liposomes and Stable Pluilamellar Vesicles," Biochemistry, vol. 24 (1985) pp. 2833-2842.
Guzman, C., et al., "Antibody Responses in the Serum and Respiratory Tract of Mice Following Oral Vaccination with Liposomes Coated with Filamentous Hemagglutinin and Pertussis Toxoid," Infection and Immunity, vol. 61, No. 2, (1993) pp. 573-579.
International Preliminary Report on Patentability for corresponding Application PCT/US2006/048770; Jan. 29, 2008.
Komatsu, H. et al., "Effects of ethanol on permeability of phosphatidylcholine/cholesterol mixed with liposomal membranes," Chemistry and Physics of Lipids, vol. 85 (1997) pp. 67-74.
Masson, G., "Characterization of Small Lipid Vesicles Prepared by Microfluidization," Progress in Colloid & Polymer Science, vol. 79, (1989) pp. 49-51.

(Continued)

*Primary Examiner* — Zohreh A Fay (74) *Attorney, Agent, or Firm* — Hemingway & Hansen, LLP; D. Scott Hemingway; Elizabeth Hartman (57) ABSTRACT

A method of encapsulating *cannabis*-derived compounds in nanosized phospholipid vesicles is disclosed. A *Cannabis sativa*-derived formulation for transmucosal and transdermal delivery comprising *Cannabis sativa*-derived compounds nanoencapsulated in phospholipid-based vesicles is also disclosed. *Cannabis sativa*-derived extracts have enhanced bioavailability when encapsulated in nanosized phospholipid vesicles prior to administration to a subject as compared to non-encapsulated cannabinoids. Also disclosed herein are methods of transmucosal and transdermal administration of the formulation having phospholipid vesicles with nanoencapsulated *Cannabis sativa*-derived substances.

20 Claims, 1 Drawing Sheet

(56) References Cited

OTHER PUBLICATIONS

Maurer, N. et al., "Spontaneous entrapment of polynucleotides upon electrostatic interaction with ethanol-destabilized cationic liposomes," Biophysical Journal, vol. 80 (2001) pp. 2310-2326.

Nounou, M. et al., "In vitro release of hydrophilic and hydrophobic drugs from liposomal dispersions and gels." Acta Pharma 56 (2006) pp. 311-324.

Panico, A. et al., "Preparation of liposome formulations containing immunomodulatory peptides." Pharmaceutica Acta Helvetiae 72 (1997) pp. 1-10.

Philippot, J.R., et al., "Liposomes as Tools in Basic Research and Industry." CRC Press, (1995) pp. 7-8.

Schnyder, A., et al., "Drug Transport to Brain with Targeted Liposomes." NeuroRx, vol. 2, No. 1 (2005) pp. 99-107.

Singh, A.K., et al., "Applications of Antibody and Fluorophore-derivatized Liposomes to Heterogeneous Immunoassays for D-dimer" Biotechnology Progress, vol. 12, No. 2 (1996) pp. 272-280.

Zheng J.Y. et al., "Pulmonary Peptide Delivery: Effect of Taste-Masking Excipients on Leuprolide Suspension Metered-Dose Inhalers," Pharmaceutical Development and Technology, vol. 6(4) (2001) pp. 521-530.

Ghaghada, Ketan, et al., "T1 Relaxivity of Core-encapsulated Gadolinium Liposomal Contrast Agents—Effects of Liposome Size and Internal Gadolinium Concentration," Acad. Radiol. (2008) 15(10), 1259-1263.

Kremer, et al., "Vesicles of Variable Diameter Prepared by Modified Injection Method," Biochemistry 16(1977) pp. 3932-3935.

Pillman et al., "Effects of Ethanol on the Organization of Phosphocholine Lipid Bilayers," J. Phy. Chem B (2010) 114, pp. 3840-3846.

Yang et al., "On the Stability of Liposomal Cantansomes in Aqueous Alcohol Solution," Langmuir (2008) pp. 1695-1700.

Zhao et al., "Size-induced Enhancement of Chemical Exchange Saturation Transfer (CEST) Contrast in Liposomes," J A. Chem Soc (2008) 130, pp. 5178-5184.

Berger, et al., "Filter extrusion of liposomes using different devices: comparisons of liposome size, encapsulation efficiency, and process characteristics," Int J Pharm, vol. 223, n.1-2 (2001), pp. 55-68.

Dos Santos, et al. "pH gradient loading of anthracyclines into cholesterol-free liposomes: enhancing drug loading rates through use of ethanol," Biochemica et Biophysica Acta 1661 (2004), pp. 47-60.

Muller, et al., "Solid lipid nanoparticles (SLN) for controlled drug delivery—a review of the state of the art," EP J of Pharma & Biopharma 50 (2000), pp. 161-177.

Karschner, Erin, et al., "Plasma Cannabinoid Pharmacokinetics following Controlled Oral delta9-Tetrahydrocannabinol and Oromucosal Cannabis Extract Administration," Clinical Chemistry, ClinicalTrials. gov, clinicaltrials.gov/ct2/show/NCT01893424. (Dec. 2010).

Karschner, Erin, et al., "Plasma Cannabinoid Pharmacokinetics following Controlled Oral delta9-Tetrahydrocannabinol and Oromucosal Cannabis Extract Administration," Clinical Chemistry 57:1, 66-75 (2011).

Schatman, Michael E., "Medical Marijuana: The State of the Science." Medscape, (Feb. 6, 2015).

Huestis, Marilyn A. "Human Cannabinoid Pharmacokinetics." Chemistry & Biodiversity, vol. 4, 1770-1804, (2007), Wiley Online Library, onlinelibrary.wiley.com/doi/10.1002/cbdv.200790152/references.

Zhornitsky, Simon, et al. "Cannabidiol in Humans—The Quest for Therapeutic Targets." Pharmaceuticals 2012, 5, 529-552; doi:1:10. 3390/ph5050529, MDPI, Molecular Diversity Preservation International, (May 21, 2012.).

Sachs, Jane, et al. "Safety and Toxicology of Cannabinoids." Neurotherapeutics, Springer New York, (Jul. 1, 2016), utah.pure. elsevier.com/en/publications/safety-and-toxicology-of-cannabinoids.

Iffland, Kerstin et al.—"An Update on Safety and Side Effects of Cannabidiol—A Review of Clinical Data and Relevant Animal Studies," Cannabis and Cannabinoid Research, vol. 2.1, 2017, (Jun. 2017), www.scribd.com/document/354665879/Update-on.Safety-and-Side-Effects-of-Cannabidiol.

Mayo Clinic, "Marijuana," Mayo Foundation for Medical Education and Research (Oct. 24, 2017), https://www.mayoclinic.org/drugs-supplements-marijuana/art-20364974.

Gerhard Nahler: "Pure Cannabidiol versus Cannabidiol-Containing Extracts: Distinctly Different Multi-Target Modulators", Alternative, Complementary & Integrative Medicine, May 29, 2018, p. 1-11, vol. 4, No. 1.

N. Grimaldi, et al: "Lipid-based nenovesicles for nanomedicine", Chemical Society Reviews, Jan. 1, 2016, p. 6520-6545, vol. 45, No. 23, UK.

METHOD OF ENCAPSULATING CANNABINOIDS IN PHOSPHOLIPID CARRIERS

CROSS REFERENCE TO RELATED APPLICATIONS

This application claims the benefit of U.S. Provisional Application No. 62/727,996 filed Sep. 6, 2018, which is incorporated by reference into this utility patent application.

STATEMENT REGARDING FEDERALLY SPONSORED RESEARCH OR DEVELOPMENT

Not applicable.

TECHNICAL FIELD OF INVENTION

The present invention relates to encapsulation of cannabinoid compounds, compositions and uses thereof.

BACKGROUND OF THE INVENTION

During most of the 20th century, the United States Food and Drug Administration ("FDA") questioned the safety of *cannabis* due to its potential for abuse, as well as the adverse cardiovascular, reproductive and pulmonary effects associated with inhalation of any type of smoke. In 1999, the Office of National Drug Control funded a study by the Institute of Medicine to evaluate medicinal uses of *cannabis*. The outcome of this 1999 study was a recommendation to test alternative cannabinoid delivery systems for medicinal use (other than inhalation of *cannabis* smoke).

Since then, a number of pharmaceutical companies have analyzed the whole plant extract (and cannabidiol (CBD) and tetrahydrocannabinol (THC)) for possible medicinal uses. Some of these extracts have been approved in Canada for neuropathic pain in multiple sclerosis and as an analgesic for cancer pain. It is currently in phase III trials in the US for a cancer pain indication.

Many studies are underway looking at the individual components of CBD and THC as well as the many specific isolates, to better define the mechanisms of action with respect to the different receptors in the body. According to the United States National Institute of Health ("NIH") there are more than 60 systematic reviews discussing the safety, toxicology, potency, and therapeutic potential of cannabinoids. Preclinical trials over the past four decades have found that the cannabinoids show promise as an anti-inflammatory, neuroprotectant, analgesic, anti-tumoral agent and anti-psychotic. Cannabidiol has also been found to be effective for control of seizures associated with certain types of epilepsy. Certain cannabinoids, like CBD, have been well-studied and are well tolerated and safe in humans, even at high doses over a period of time.

*Cannabis sativa* has over 483 known compounds, over 60 of which are classified as cannabinoids, many of which have mental and physical effects, including tetrahydrocannabinol (THC) and cannabidiol (CBD). Cannabidiol (CBD) is one of the most prevalent chemical compounds in the *cannabis* plant. Among the other *cannabis*-derived compounds are a variety of terpenes. These terpenes are oils secreted from the plant which give the plant its characteristic odor. Terpenes produce physical effects similar to those seen with CBD.

Hemp is a variety of the *Cannabis sativa* plant species that is grown specifically for the industrial uses of its derived products. Although *cannabis* used as a drug and hemp for industrial use both derive from the species *Cannabis sativa* and contain tetrahydrocannabinol (THC), the strains are distinct and have unique phytochemical compositions and uses. Hemp has lower concentrations of THC and higher concentrations of cannabidiol (CBD), which decreases or eliminates its psychoactive effects. The higher concentrations of cannabidiol and lower concentrations of THC make hemp an ideal source for extraction of CBD.

THC is the primary compound associated with *cannabis* psychoactive effects, while CBD does not appear to have psychoactive effects. Unlike THC, CBD is non-psychoactive, but still has an effect on the body. The THC portion of the plant is the psychoactive ingredient and therefore progressing the use of medical CBD alone is viewed as viable.

When considering the medical use of a Cannabidiol (CBD) substance, the bioavailability of the CBD substance is the degree and rate at which the CBD is absorbed into the body or is made available at the site of physiological activity. This degree and rate of absorption is an essential determining factor as to the efficacy of the drug. There has been very little comparable testing done on the bioavailability of CBD through the different modes of administration in humans, and it is critical to gain an understanding of the pharmacokinetics of CBD to ensure that it is controlled and understood for each route of administration and any specific indications.

Even though oral administration of CBD has shown anecdotal positive effects, the bioavailability of oral CBD administrated substances appears to be very low (~6%-15%) due to the "first pass" metabolism." There is also been shown to be a great variation from individual to individual in the absorption rates for oral CBD administrated substances, with the effects generally lasting between 5-8 hours resulting in a lower re-medication rate. Sublingual (under the tongue) and buccal (cheek or gums) have shown similar bioavailability results to oral administration. While sublingual or buccal is not as fast acting as smoking/vaporizing, it is considered a much safer option than smoking.

Studies have shown oromucosal bioavailability to be approximately 35% bioavailability. With the exception of intravenous (IV) application, smoking and vaporizing shows the highest bioavailability in the shortest amount of time and as such becomes the target standard to achieve by a different route of administration (2%-56% with average around 40%); however, the length of time CBD remains in the body via this route is only around 3 hours. Smoking and vaporizing has historically been the route of administration for experienced users, but is not considered the most acceptable route of administration due to exposure to the adverse health consequences of inhaling smoke in the lungs. These adverse health impacts that arise with smoking and vaporizing make it an unhealthy choice for the administration of a CDB substance.

Recent studies have suggested a clear role for CBD as a medical therapy for many disorders; however, the route of administration severely impacts the bioavailability of the CBD, and in all acceptable cases the bioavailability remains low. A route of administration that is safe and controlled, that reaches the bloodstream as quickly as smoking, has the highest peak value, and remains in the bloodstream for the longest time is needed.

SUMMARY OF THE INVENTION

Disclosed herein is a method of making a combination of nano-encapsulated cannabidiol (CBD) and non-CBD *Cannabis sativa*-derived substances. The combination is made by preparing a first CBD *cannabis* vesicle solution having a first plurality of phospholipid vesicles that contain a nano-encapsulated cannabidiol (CBD), a second non-CBD *cannabis* vesicle solution having a second plurality of phospholipid vesicles that contain a nano-encapsulated non-CBD *Cannabis sativa*-derived substance, combining the first CBD *cannabis* vesicle solution with the second non-CBD *cannabis* vesicle solution to produce a combined *cannabis* vesicle solution, adding a quantity of water having a pH of 6-8 to the combined *cannabis* vesicle solution; and mixing the combined *cannabis* vesicle solution with the quantity of water to nano-encapsulate the CBD and non-CBD *Cannabis sativa* derived substances in the combined vesicle solution into phospholipid vesicles sized from 25 nm to 200 nm to produce the combination of nano-encapsulated cannabidiol (CBD) and non-CBD *Cannabis sativa*-derived substances.

The first CBD *cannabis* vesicle solution having a first plurality of phospholipid vesicles that contain a nano-encapsulated cannabidiol (CBD) is prepared by the following steps. The first *cannabis* CBD solution is formed by preparing a cannabidiol (CBD) substance derived from *Cannabis sativa*; dissolving the CBD substance in a first quantity of ethanolic solution having ethanol, phospholipids and water to produce a first CBD-ethanolic solution, with the ethanolic solution having one or more phospholipid vesicles. The first CBD-ethanolic solution is then diluted with a first quantity of ethanol to produce a first diluted CBD-ethanolic solution, and the first diluted CBD-ethanolic solution is mixed to incorporate the CBD into the first plurality of phospholipid vesicles sized less than 10 nm to produce the first CBD *cannabis* vesicle solution.

The second non-CBD *cannabis* vesicle solution having a second plurality of phospholipid vesicles that contain a nano-encapsulated non-CBD *Cannabis sativa*-derived substance is prepared by the following steps. The second non-CBD *cannabis* solution is formed by preparing a non-CBD substance derived from *Cannabis sativa*; dissolving the non-CBD *Cannabis sativa*-derived substance in a second quantity of ethanolic solution having ethanol, phospholipids and water to produce the second non-CBD *cannabis* solution with the ethanolic solution having one or more phospholipid vesicles; diluting the second non-CBD *cannabis*-ethanolic solution with a second quantity of ethanol to produce a second diluted non-CBD *cannabis*-ethanolic solution, and mixing the second diluted non-CBD *cannabis*-ethanolic solution to incorporate the non-CBD *Cannabis sativa*-derived substance into the second plurality of phospholipid vesicles sized less than 10 nm to produce the second non-CBD *cannabis* vesicle solution.

The first CBD *cannabis* vesicle solution having a first plurality of phospholipid vesicles that contain a nano-encapsulated cannabidiol (CBD) and the second non-CBD *cannabis* vesicle solution having a second plurality of phospholipid vesicles that contain a nano-encapsulated non-CBD *Cannabis sativa*-derived substance are combined to produce a combined *cannabis* vesicle solution; a quantity of water having a pH of 6-8 is added to the combined *cannabis* vesicle solution; and the combined *cannabis* vesicle solution is mixed with a quantity of water to nano-encapsulate the CBD and non-CBD *Cannabis sativa* derived substances in the combined vesicle solution into phospholipid vesicles sized from 25 nm to 200 nm to produce the combination of nano-encapsulated cannabidiol (CBD) and non-CBD *Cannabis sativa*-derived substances.

The non-CBD *Cannabis sativa*-derived substance may be tetrahydrocannabinol (THC), *Cannabis sativa*-derived terpenes, *Cannabis sativa*-derived flavonoids, a whole plant extract of *Cannabis sativa*, or combinations thereof. Optionally, a non-*cannabis* substance may be dissolved in the quantity of water prior to combining with the combined *cannabis* vesicle solution.

The concentration range of CBD in the first *cannabis* solution may be from 1 part CBD to 10 parts of the first quantity of ethanolic solution up to 10 parts CBD to 1 part of the first quantity of ethanolic solution (w/w), and the concentration of non-CBD *Cannabis sativa* derived substance in the second *cannabis* solution may be from 1 part non-CBD *Cannabis sativa*-derived substance to 10 parts of the second quantity of the ethanolic solution up to 10 parts non-CBD *Cannabis sativa*-derived substance to 1 part of the second quantity of the ethanolic solution (w/w).

The first and second quantities of ethanolic solutions have 75-89% ethanol, 10-20% phospholipids and 1-5% water (w/w) and phosphatidylcholine (PC) is at least 50% of the phospholipid total in the first and second quantities of ethanolic solutions.

Also disclosed is a method of making one or more nano-encapsulated *Cannabis sativa*-derived substances. The one or more nano-encapsulated *Cannabis sativa*-derived substances are made by preparing a *Cannabis sativa*-derived substance; preparing an ethanolic solution having ethanol, phospholipids, and water, said ethanolic solution having one or more phospholipid vesicles; dissolving the *Cannabis sativa*-derived substance in the ethanolic solution to produce a *cannabis* solution; diluting the *cannabis* solution with a quantity of ethanol to produce a first diluted *cannabis* solution; combining the first diluted *cannabis* solution with a quantity of water having a pH of 6-8 to produce a second diluted *cannabis* solution; and mixing the second diluted *cannabis* solution to encapsulate the *Cannabis sativa* derived substance in the one or more phospholipid vesicles to produce one or more nano-encapsulated *Cannabis sativa* derived substances. The phospholipid vesicles with nano-encapsulated *Cannabis sativa*-derived substance are sized from 25 nm to 200 nm.

*Cannabis sativa*-derived substances are selected from cannabidiol (CBD), tetrahydrocannabinol (THC), *Cannabis sativa*-derived terpenes, *Cannabis sativa*-derived flavonoids, a whole plant extract of *Cannabis sativa*, and combinations thereof. Optionally, the *Cannabis sativa*-derived substance is cannabidiol (CBD), tetrahydrocannabinol (THC) or a combination of cannabidiol (CBD) and tetrahydrocannabinol (THC). The *cannabis* solution has a concentration range from 1 part *Cannabis sativa*-derived substance to 10 parts ethanolic solution up to 10 parts *Cannabis sativa*-derived substance to 1 part ethanolic solution (w/w).

The ethanolic solution has 75-89% ethanol, 10-20% phospholipids and 1-5% water (w/w), and optionally, phosphatidylcholine (PC) is at least 50% of the phospholipid total in the ethanolic solution. Optionally, the quantity of ethanol combined with the *cannabis* solution is at a ratio of 1:1 to 1:10 parts of *cannabis* solution to ethanol (by volume), and the quantity of water combined with the first diluted *cannabis* solution is at a ratio from 1:5 to 1:25 parts of diluted *cannabis* solution to water (by volume). Optionally, a non-*cannabis* substance is dissolved in the quantity of water prior to combining with the diluted *cannabis* solution.

The present invention is a composition formulated from a *Cannabis sativia*-derived substance for transmucosal and transdermal delivery using encapsulation in phospholipid carriers. *Cannabis sativa*-derived substances for encapsulation are selected from cannabidiol (CBD), tetrahydrocannabinol (THC), *Cannabis sativa*-derived terpenes, *Cannabis sativa*-derived flavonoids, a whole plant extract of *Cannabis*

*sativa*, and combinations thereof. The *Cannabis sativa*-derived substance may be cannabidiol (CBD). The *Cannabis sativa*-derived substance may be tetrahydrocannabinol (THC). The *Cannabis sativa*-derived substance may be a combination of cannabidiol (CBD) and tetrahydrocannabinol (THC). The *Cannabis sativa*-derived substance may be a whole plant extract of *Cannabis sativa*.

The composition formulated for transmucosal or transdermal delivery of *Cannabis sativa* derived substances in the present invention is formulated to be encapsulated in a phospholipid delivery system. For the present invention, one or more *Cannabis sativa*-derived substance is nanoencapsulated in phospholipid vesicles having phospholipids, ethanol and water. The phospholipid vesicles having the encapsulated *Cannabis sativa*-derived substance are sized from 25 nm to 200 nm. Phosphatidylcholine comprises at least 50% by weight of the phospholipids in the phospholipid vesicles. The concentration range of *Cannabis sativa*-derived substance encapsulated in the phospholipid vesicles is from 0.01% to 1.0% w/w.

For transmucosal administration, the phospholipid vesicles with the nanoencapsulated *Cannabis sativa*-derived substance are administered to the oral cavity of a subject for transmucosal uptake of the *Cannabis sativa*-derived substance. Transmucosal delivery can be via liquids such as drops, sprays, aerosols or shots, gels, pastes, lozenges, gums, gummy candies, hard candies, orally dissolving strips, tablets, swish and swallow preparations, or other form suitable for contact to oral mucosa. For transdermal administration, the phospholipid vesicles with the nanoencapsulated *Cannabis sativa*-derived substance are applied to the epidermis of a subject for transdermal uptake of the *Cannabis sativa*-derived substance. Transdermal delivery can be via a topically applied preparation, such as a cream, lotion, ointment, wax, topically applied spray, gel, balm, transdermal patch or other transdermal application means.

DETAILED DESCRIPTION

Disclosed herein is a composition comprising *Cannabis sativa*-derived substances encapsulated in a phospholipid delivery system. The *Cannabis sativa*-derived substances for encapsulation are selected from cannabidiol (CBD), tetrahydrocannabinol (THC), *Cannabis sativa*-derived terpenes, *Cannabis sativa*-derived flavonoids, a whole plant extract of *Cannabis sativa*, and combinations thereof.

*Cannabis sativa*-derived substances for encapsulation may be cannabidiol (CBD), tetrahydrocannabinol (THC), or cannabidiol (CBD) and tetrahydrocannabinol (THC). The *Cannabis sativa*-derived substances can be derived from all varieties of *Cannabis sativa*, including hemp. *Cannabis* varieties used for hemp production are one preferred source of CBD because of a high concentration of CBD with a low concentration of THC in materials from those plants.

*Cannabis*-derived compounds can be extracted from plant parts of *Cannabis sativa*, either from marijuana grade *Cannabis* or from industrial grade hemp. There are numerous *Cannabis*-derived compounds with the most prevalent being cannabinoids, such as cannabidiol (CBD) and tetrahydrocannabinol (THC), terpenes and flavonoids. CBD and THC are the best known of the *cannabis*-derived compounds and both have been studied for medical applications.

The *cannabis*-derived compounds are extracted from plant parts of *Cannabis sativa*. For use in the claimed invention, *cannabis*-derived compounds can be extracted from *Cannabis* plants having 0.3% tetrahydrocannabinol (THC) or less in the leaves and flowering heads (industrial hemp), from *Cannabis* plants having more than 0.3% tetrahydrocannabinol (THC) in the leaves and flowering heads, from the whole *cannabis* plant, or any combination thereof.

The *cannabis*-derived compounds can be extracted from the *Cannabis* plant parts using solvents such as butane, propane or ethanol, or by using a super-critical $CO_2$ extraction process. CBD can be derived from *cannabis* or hemp plant parts by extraction processes, including organic solvent extraction using one or more organic solvent, including, but not limited to, butane, propane and alcohols, with ethanol the preferred alcohol. Solvent-free CBD can be derived from *cannabis* or hemp plant parts by a super-critical $CO_2$ extraction process. CBD extracts useful for the claimed invention are in a liquid, oil or crystalline form.

Solvent directed processes, such as butane or propane extraction, must be purged of residual solvent prior to use. Ethanol is often used as an extraction solvent because the ethanol does not require purging to remove the ethanol, as do butane or propane. The composition of the extracts will vary based on the type of solvent used, with solvents such as butane and propane extracting only lipid soluble compounds, while alcohols extract both lipid and water soluble compounds. Extracts produced by solvent extraction typically have an oily or waxy consistency and may require additional processing to remove impurities.

Supercritical $CO_2$ extraction uses phase changes in carbon dioxide, utilizing temperature and pressure, to produce an extract having a high purity that does not require purging to remove solvent residues. Because $CO_2$ does not leave residues in the extracted materials, the super-critical $CO_2$ extraction process yields an extract with greater than 99% purity that is free of solvent residues. Extracts produced by $CO_2$ extraction are a white needle-like crystalline powder.

THC can also be extracted from *cannabis* or hemp plant parts by extraction using an organic solvent, such as butane, propane or ethanol, or by the super-critical $CO_2$ extraction process. Additionally, solvents such as polyethylene glycol 400 (PEG 400), glycerin, or oelic acid can be used instead of or in addition to the butane, propane and ethanol solvent processes. Oils are the most commonly available form for THC extracts.

Terpenes and flavonoids are *cannabis*-derived compounds that can also be extracted from *cannabis* plant parts using butane, propane, ethanol or $CO_2$ extraction processes. Terpenes are aromatic compounds and flavonoids are phytonutrients, and these *cannabis*-derived compounds can be used as isolates or in combination with the CBD and/or THC cannabinoids. Terpenes and flavonoids work synergistically with cannabinoids to produce variations in benefits and side effects associated with the cannabinoids.

Cannabinoids other than CBD and THC can be derived from *Cannabis sativa* and may also be used in the disclosed invention. Most of the other cannabinoids are non-psychoactive or mildly psychoactive, and many have physiological effects similar to the effects seen for CBD. These other cannabinoids may work synergistically to enhance the effects of CBD and THC.

Additional cannabinoids that may be used in the disclosed invention include, but are not limited to: Cannabigerol CBG), Cannabidiolic Acid CBDA), Tetrahydrocannabinolic Acid (THCA), Cannabinol (CBN), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol monomethyl ether (CBGM), Cannabielsoin (CBE), Cannabicitran (CBT), and combinations thereof. Whole plant extracts of *Cannabis sativa* may also be used in the disclosed invention.

CBD and THC extracts can be used in combination in the nanosized phospholipid vesicle composition. CBD and THC are extracted from *cannabis* plants as separate isolates, either as oils or crystals, and then combinations of these extracts can be encapsulated in the phospholipid vesicles. Whole plant *cannabis* extracts can also be encapsulated in the nanosized phospholipid vesicles. Whole plant *cannabis* extract is an oily or waxy material that is soluble in lipids and alcohols. Whole plant extracts will vary in the amount of cannabinoids in the extract depending on whether the extract is prepared from marijuana-grade *cannabis* or industrial-grade hemp. Both types of whole plant extracts will have cannabinoids, terpenes and flavonoids, with the primary difference being the concentrations of CBD and THC in the final extract.

Nano-encapsulated CBD has a greater bioavailability than the equivalent, non-encapsulated form of a CBD substance, thus reducing the need for frequent re-medication, while providing a greater bioavailability, greater active duration and a greater ease of use resulting in increased compliance. That is, one way to enhance the bioavailability of CBD and other cannabinoids is to use nano-encapsulation of the CBD formulation using phospholipid vesicles.

Phospholipid vesicles are very similar to structures that the body naturally produces with phospholipid vesicles being tiny hollow spheres that have the ability to carry both water soluble and fat soluble compounds through the body and cell membranes. Encapsulating cannabinoids in this manner would allow the cannabinoids to enter the bloodstream at a much greater bioavailability than a non-encapsulated form of the same therapeutic compounds. Phospholipid nano-encapsulation has shown promise in enhancing the speed of absorption as well as overall bioavailability of *Cannabis sativa*-derived substances.

A single dose of CBD in its nano-encapsulated form (using transdermal and sublingual administration methods) will reach the bloodstream faster, have a higher peak availability, and remain in the bloodstream longer, than its non-encapsulated counterpart. Nano-encapsulation technology is safe and has been for used successfully for topical drug delivery and oral nutritional delivery in human subjects. The nano-encapsulation technique enhances the bioavailability, uptake, and sustainability of the cannabinoids in the body.

Multiple routes of administration have been used for *Cannabis sativa*-derived substances with transmucosal and transdermal routes preferred for cannabinoids nanoencapsulated in phospholipid vesicles. A CBD amount of ~10 mg is generally considered a "starting dose" by the medical community, with amounts typically going up to 300 mg daily for specific disease states. *Cannabis sativa*-derived substances which are nanoencapsulated in phospholipid vesicles can be administered in dosages ranging from 1 mg to 300 mg per day in single or divided doses. Optionally, dosages range from 10 mg to 100 mg per day in single or divided doses.

Disclosed herein is a composition comprising one or more *Cannabis sativa*-derived substance nanoencapsulated in phospholipid vesicles having phospholipids, ethanol and water. The phospholipid vesicles having the encapsulated *Cannabis sativa*-derived substance are sized from 25 nm to 200 nm. Phosphatidylcholine comprises at least 50% by weight of the phospholipids in the phospholipid vesicles. The concentration range of *Cannabis sativa*-derived substance encapsulated in the phospholipid vesicles is from 0.01% to 1.0% w/w.

*Cannabis*-derived extracts have enhanced bioavailability when encapsulated in nanosized phospholipid vesicles prior to administration to a subject as compared to non-encapsulated cannabinoids. Also disclosed herein is a method of using the composition having nano-encapsulated *cannabis*-derived compounds to administer the *cannabis*-derived active compounds to a subject in need of treatment. *Cannabis*-derived substances encapsulated in nanosized phospholipid vesicles can be advantageously administered through transmucosal and transdermal routes.

A delivery option comprising encapsulating one or more *cannabis*-derived compounds as passenger molecules in a potentiated nanolipidic process capable of delivering the *cannabis*-derived compound to a subject is disclosed. The route of delivery can be oral transmucosal (including sublingual and buccal) or transdermal.

Disclosed herein is a composition formulated for transmucosal delivery of *Cannabis sativa* derived substances encapsulated in a phospholipid delivery system. *Cannabis sativa*-derived substances for encapsulation are selected from cannabidiol (CBD), tetrahydrocannabinol (THC), *Cannabis sativa*-derived terpenes, *Cannabis sativa*-derived flavonoids, a whole plant extract of *Cannabis sativa*, and combinations thereof. Oral delivery can be via a transmucosal preparation, a sublingual/buccal preparation, or a preparation administered to the oral cavity. Transmucosal preparations can be liquids such as drops, sprays, aerosols or shots, gels, pastes, lozenges, gums, gummy candies, hard candies, orally dissolving strips, tablets, swish and swallow preparations, or other form suitable for contact to oral mucosa. The preparation may be applied to the mucosa under the tongue (sublingual), inside the cheeks (buccal), or placed inside the oral cavity.

Also disclosed herein is a composition formulated for transdermal delivery of *Cannabis sativa* derived substances encapsulated in a phospholipid delivery system. *Cannabis sativa*-derived substances for encapsulation are selected from cannabidiol (CBD), tetrahydrocannabinol (THC), *Cannabis sativa*-derived terpenes, *Cannabis sativa*-derived flavonoids, a whole plant extract of *Cannabis sativa*, and combinations thereof. For transdermal administration, the phospholipid vesicles with the nanoencapsulated *Cannabis sativa*-derived substance are applied to the epidermis of a subject for transdermal uptake of the *Cannabis sativa*-derived substance. Transdermal delivery can be via a topically applied preparation, such as a cream, lotion, ointment, wax, topically applied spray, gel, balm, transdermal patch or other transdermal application means.

Disclosed is a method of nano-encapsulating a *Cannabis sativa*-derived substance including the steps of preparing a *cannabis* stock by dissolving a *Cannabis sativa*-derived substance in an ethanolic stock having phospholipids, ethanol and water; diluting the *cannabis* stock with a quantity of ethanol; combining the diluted *cannabis* stock with a quantity of purified water having a pH of 6-8; and mixing the diluted *cannabis* stock/water combination vigorously to encapsulate the *Cannabis sativa* derived substance in one or more phospholipid vesicle.

*Cannabis sativa*-derived substances for the disclosed encapsulation method are selected from cannabidiol (CBD), tetrahydrocannabinol (THC), *Cannabis sativa*-derived terpenes, *Cannabis sativa*-derived flavonoids, a whole plant extract of *Cannabis sativa*, and combinations thereof. The *Cannabis sativa*-derived substance may be cannabidiol (CBD). The *Cannabis sativa*-derived substance may be tetrahydrocannabinol (THC). The *Cannabis sativa*-derived substance may be a combination of cannabidiol (CBD) and tetrahydrocannabinol (THC). The *Cannabis sativa*-derived substance may be a whole plant extract of *Cannabis sativa*.

The ethanolic stock in the disclosed nano-encapsulation method has 75-89% ethanol, 10-20% phospholipids and 1-5% water (w/w). In the present method, phosphatidylcholine (PC) is at least 50% of the phospholipid total in the ethanolic stock. In the present method, the phospholipid vesicles with nanoencapsulated *Cannabis sativa*-derived substance are sized from 25 nm to 200 nm. In the present method, the *cannabis* stock has a concentration range from 1 part *Cannabis sativa*-derived substance to 10 parts ethanolic stock up to 10 parts *Cannabis sativa*-derived substance to 1 part ethanolic stock (w/w). In the present method, the quantity of ethanol combined with the *cannabis* stock is at a ratio of 1:1 to 1:10 parts of *cannabis* stock to ethanol (by volume). In the present method, the quantity of water combined with the diluted *cannabis* stock is at a ratio from 1:5 to 1:25 parts of diluted *cannabis* stock to water (by volume).

Disclosed is a method of preparing lipid vesicles nanoencapsulating *Cannabis sativa* derived substances comprising the steps of preparing a plurality of non-spherical phospholipid vesicles having nanoencapsulated cannabidiol (CBD) derived from *Cannabis sativa* by dissolving CBD in an ethanolic stock having 75-89% ethanol, 10-20% phospholipids and 1-5% water (w/w), diluting the CBD-ethanol stock with a quantity of ethanol, and mixing the diluted CBD-ethanol stock combination to incorporate the CBD in said plurality of non-spherical phospholipid vesicles, said vesicles sized less than 10 nm; adding a quantity of purified water having a pH of 6-8 to the plurality of non-spherical phospholipid vesicles; and mixing said plurality of non-spherical phospholipid vesicles vigorously with said quantity of water to encapsulate the CBD in spherical phospholipid vesicles sized from 25 nm to 200 nm. A non-*cannabis* substance may optionally be dissolved in the quantity of water prior to combining with the diluted *cannabis* stock.

Disclosed is a method of preparing lipid vesicles nanoencapsulating *Cannabis sativa* derived substances comprising the steps of preparing a first plurality of non-spherical phospholipid vesicles having nanoencapsulated cannabidiol (CBD) derived from *Cannabis sativa* by dissolving CBD in an ethanolic stock having 75-89% ethanol, 10-20% phospholipids and 1-5% water (w/w), diluting the CBD-ethanol stock with a quantity of ethanol, and mixing the diluted CBD-ethanol stock combination to incorporate the CBD in said first plurality of non-spherical phospholipid vesicles, said vesicles sized less than 10 nm; preparing a second plurality of non-spherical phospholipid vesicles nanoencapsulating a non-CBD *Cannabis sativa* derived substance by dissolving the non-CBD *Cannabis sativa* derived substance in an ethanolic stock having 75-89% ethanol, 10-20% phospholipids and 1-5% water (w/w), diluting the non-CBD *cannabis*-ethanol stock with a quantity of ethanol, and mixing the diluted non-CBD *cannabis*-ethanol stock combination to incorporate the non-CBD *Cannabis sativa* in said second plurality of non-spherical phospholipid vesicles, said vesicles sized less than 10 nm; combining said first plurality of non-spherical phospholipid vesicles with said second plurality of non-spherical phospholipid vesicles; adding a quantity of purified water having a pH of 6-8 to the combined first and second plurality of non-spherical phospholipid vesicles; and mixing said combined first and second plurality of non-spherical phospholipid vesicles vigorously with said quantity of water to encapsulate the CBD and non-CBD *Cannabis sativa* derived substances in spherical phospholipid vesicles sized from 25 nm to 200 nm. A non-*cannabis* substance may dissolved in the quantity of water prior to combining with the diluted *cannabis* stock.

A method for administration of a *Cannabis sativa*-derived substance comprising the steps of: providing a preparation having one or more *Cannabis sativa*-derived substance, nanoencapsulated in one or more phospholipid vesicles having phospholipids, ethanol, and water, and having a *Cannabis sativa*-derived substance concentration of 0.01% to 1.0% w/w; and administering a quantity of the preparation having 1 mg to 100 mg of *Cannabis sativa*-derived substance to a subject in need of treatment. The *Cannabis sativa*-derived substance is selected from cannabidiol (CBD), tetrahydrocannabinol (THC), *Cannabis sativa*-derived terpenes, *Cannabis sativa*-derived flavonoids, a whole plant extract of *Cannabis sativa*, and combinations thereof. The *Cannabis sativa*-derived substance may be cannabidiol (CBD), tetrahydrocannabinol (THC) or a combination of cannabidiol (CBD) and tetrahydrocannabinol (THC).

In the disclosed method, the preparation having one or more *Cannabis sativa*-derived substance nanoencapsulated in one or more phospholipid vesicles may be applied to an oral mucosa area of the subject and the preparation is kept in contact with the oral mucosa for 1 minute to 10 minutes or the preparation having one or more *Cannabis sativa*-derived substance nanoencapsulated in one or more phospholipid vesicles may be applied to an epidermal area of the subject and the preparation is kept in contact with the epidermal area for 1 minute to 24 hours. Transmucosal preparations can be liquids such as drops, sprays, aerosols or shots, gels, pastes, lozenges, gums, gummy candies, hard candies, orally dissolving strips, tablets, swish and swallow preparations, or other form suitable for contact to oral mucosa. The preparation may be applied to the mucosa under the tongue (sublingual), inside the cheeks (buccal), or placed inside the oral cavity. Transdermal delivery can be via a topically applied preparation, such as a cream, lotion, ointment, wax, topically applied spray, gel, balm, transdermal patch or other transdermal application means A method is disclosed for intraoral transmucosal administration of a *Cannabis sativa*-derived substance comprising the steps of: providing a preparation having one or more *Cannabis sativa*-derived substance selected from cannabidiol (CBD), tetrahydrocannabinol (THC), *Cannabis sativa*-derived terpenes, *Cannabis sativa*-derived flavonoids, a whole plant extract of *Cannabis sativa*, and combinations thereof, nanoencapsulated in one or more phospholipid vesicles, said one or more phospholipid vesicle having phospholipids, ethanol and water; applying a quantity of the preparation having from 1 mg to 100 mg to the subject's oral mucosa; and allowing the preparation to remain in contact with the mucosa for a period of time ranging from 1 minute to 10 minutes or may be kept in contact for 1 minute to 5 minutes. The preparation may be applied to intraoral mucosa, including sublingual and buccal mucosa. The preparation of nanosized phospholipid vesicles has a *Cannabis sativa*-derived substance concentration of 0.01% to 1.0% w/w, the phospholipid vesicles with nanoencapsulated *Cannabis sativa*-derived substance are sized from 25 nm to 200 nm, and phosphatidylcholine (PC) is at least 50% of the phospholipid total in the phospholipid vesicles.

A method for transdermal administration of a *Cannabis sativa*-derived substance comprising the steps of: providing a preparation of a *Cannabis sativa*-derived substance nanoencapsulated in one or more phospholipid vesicle having phospholipids, ethanol and water; applying a quantity of the preparation having from 1 mg to 100 mg to an area of the subject's epidermis; and allowing the preparation to remain in contact the epidermis for a period of time ranging from 1 minute to 24 hours. The *Cannabis sativa*-derived substance applied to the epidermis may be cannabidiol (CBD), tetrahydrocannabinol (THC), or a combination of cannabidiol (CBD) and tetrahydrocannabinol (THC). The preparation is applied via a cream, lotion, ointment, wax, gel, balm, spray or transdermal patch.

To prepare the nanoencapsulated cannabinoids, the *cannabis*-derived extracts are first dissolved in an ethanolic stock comprising ethanol, phospholipids and water. Phospholipids are combined with ethanol and stirred at ambient room temperature until dissolved. Optionally, the ethanol used in the ethanolic stock is dehydrated 190 proof ethanol. A small quantity of water having a pH of 6-8 is added to the ethanol/phospholipid mixture and stirred until an optically clear ethanolic stock is formed. The ratio of the components in the ethanolic stock has a range of 75-89% ethanol, 10-20% phospholipids and 1-5% water, with a preferred ratio of 80% ethanol/17.75% phospholipids/2.25% water (w/w). Optionally, the phospholipids are derived from soy lecithin. The phospholipids are selected from phosphatidylcholine (PC), phosphatidylethanolamine (PE), phosphatidic acid (PA) and phosphatidylinositol (PI), and mixtures thereof. Optionally, phosphatidylcholine (PC) comprises at least 50% by weight of the phospholipid mixture. Optionally, phosphatidylcholine comprises 65% of the phospholipid total.

A *cannabis* stock is prepared by combining the ethanolic stock with one or more *cannabis*-derived extract and mixed at ambient room temperature until the extract is completely dispersed in the ethanolic stock. The ratio range of *cannabis*-derived extract to ethanolic stock is from 1 part *cannabis*-derived extract to 20 parts ethanolic stock to 20 parts *cannabis*-derived extract to 1 part ethanolic stock. Optionally, the ratio range of *cannabis*-derived extract to ethanolic stock is from 1 part *cannabis*-derived extract to 10 parts ethanolic stock to 10 parts *cannabis*-derived extract to 1 parts ethanolic stock. In one embodiment, the ratio of *cannabis*-derived extract to ethanolic stock is 1:1. Optionally, the ratio of *cannabis*-derived extract to ethanolic stock is any ratio between 0.5 g:4.5 g and 4.5 g:0.5 g. In one embodiment, the ratio of *cannabis*-derived extract to ethanolic stock is 1:1. In another embodiment, the ratio of *cannabis*-derived extract to ethanolic stock is 0.5 g:4.5 g. In another embodiment, the ratio of *cannabis*-derived extract to ethanolic stock is 4.5 g:0.5 g. Mixing of *cannabis*-derived extract into the ethanolic stock may be with a vortex, a magnetic stir-bar, an overhead mixer or a propeller type mixer.

Following preparation of the *cannabis* stock, a quantity of ethanol is added to the *cannabis* stock and thoroughly mixed at room temperature. Optionally, the additional quantity of ethanol is mixed with the *cannabis* stock using a vortex, a magnetic stir bar, or an overhead mixer. This dilution with ethanol can range from 1:1 to 1:100 by volume, with 1 to 100 parts of ethanol added to 1 part of the *cannabis* stock, inclusive of any amount between 1 and 100 parts of ethanol being added to 1 part of the *cannabis* stock. Optionally, the *cannabis* stock is combined with the ethanol at a ratio of 1:25 by volume. Optionally, the *cannabis* stock is combined with the ethanol at a ratio of 1:10 by volume. Optionally, the ethanol is added to the *cannabis* stock with the ethanol at 1:5 by volume. Optionally, the *cannabis* stock is combined with the ethanol at a ratio of 1:2.5 by volume. Optionally, the *cannabis* stock is combined with the ethanol at a ratio of 1:1 by volume. The secondary addition of ethanol adjusts the size of the lipid vesicles with the vesicle size decreasing as the amount of ethanol added increases. Following the addition of the secondary quantity of ethanol, the vesicles are less than 10 nm diameter and have not attained a spherical shape.

A quantity of an aqueous solvent comprising distilled or deionized water having a pH of 6-8 is added to the ethanol-diluted *cannabis* stock and thoroughly mixed at ambient room temperature until a uniform composition having an opalescent appearance is achieved. Optionally, the aqueous solvent is mixed with the ethanol-diluted *cannabis* stock using a vortex, a magnetic stir bar, or an overhead mixer.

This addition of aqueous solvent can range from 1:1 to 1:100 by volume, with 1 to 100 parts of aqueous solvent added to 1 part of the ethanol-diluted *cannabis* stock, inclusive of any amount between 1 and 100 parts of aqueous solvent being added to the ethanol-diluted *cannabis* stock. Optionally, the ratio is from 1:1 to 1:25 parts of ethanol-diluted *cannabis* stock to aqueous solvent. Optionally, the ratio is from 1:5 to 1:25 parts of ethanol-diluted *cannabis* stock to aqueous solvent. Optionally, the ratio is 1:9 parts of ethanol-diluted *cannabis* stock to aqueous solvent.

Secondary passenger substances can be dissolved in the aqueous solvent prior to combining with ethanol-diluted *cannabis* stock. Optionally, secondary passengers are water soluble *cannabis*-derived extracts. Optionally, the secondary passengers are non-*cannabis* substances. Non-*cannabis* substances are substances that can be used advantageously to enhance the usability of the nanosized phospholipid vesicles. Optionally, the substances enhance usability of the nanosized phospholipid vesicles as flavoring agents, masking agents, penetrating agents, augmenting agents, synergistic agents, or other agents to improve application and bioavailability of the encapsulated passenger.

Spherical nanosized phospholipid vesicles result in the opalescent composition when the aqueous solvent is fully combined with the ethanol-diluted *cannabis* stock. The opalescent composition has spherical nanosized phospholipid vesicles that are sized from 25 nm to 200 nm in diameter. Optionally, the vesicles are sized from 80 nm to 100 nm. Optionally, the vesicles are about 80 nm in diameter.

Cannabinoid compounds incorporated in the ethanol-diluted *cannabis*-derived extract/ethanolic stock have a concentration range of 0.1%40% (w/w). Following 1:10 dilution with the aqueous solvent, the nanosized phospholipid vesicles have a concentration of 0.01% to 1.0% (w/w). Optionally, the concentration of cannabinoid compounds incorporated in the ethanol-diluted *cannabis*-derived extract/ethanolic stock is from 1% to 2%. Optionally, following 1:10 dilution with the aqueous solvent, the nanosized phospholipid vesicles have a cannabinoid compound concentration from 0.1% to 0.2% (w/w).

A *cannabis* stock having CBD is prepared by combining a crystalline CBD isolate having greater than 99% purity with ethanolic stock at a concentration range of 0.1%40% (w/w) and mixed at ambient room temperature until completely dissolved. The *cannabis* stock is then combined with a quantity of ethanol, 1:1 to 1:100 (by volume) and stirred until the mixture is homogenous. The ethanol-diluted *cannabis* stock is then combined with a quantity of aqueous solvent, 1:1 to 1:100 (by volume) and mixed until a uniform composition having an opalescent appearance is achieved. The opalescent composition has nanosized spherical phospholipid vesicles that are from 25 nm to 200 nm in diameter. Optionally, the vesicles are sized from 80 nm to 100 nm. Optionally, the vesicles are about 80 nm in diameter.

A *cannabis* stock having THC is prepared by combining THC oil at a concentration range of 0.1%40% (w/w) with ethanolic stock and mixed at ambient room temperature until completely dissolved. The *cannabis* stock is then combined with a quantity of ethanol, 1:1 to 1:100 (by volume), and stirred until the mixture is homogenous. The ethanol-diluted *cannabis* stock is combined with a quantity of water, 1:1 to 1:100 (by volume), and mixed until a uniform composition having an opalescent appearance is achieved. The opalescent composition has nanosized spherical phospholipid vesicles that are from 25 nm to 200 nm in diameter. Optionally, the vesicles are sized from 80 nm to 100 nm. Optionally, the vesicles are about 80 nm in diameter.

Combinations of CBD and THC, at a concentration range of 0.1%-10% (w/w) of combined cannabinoids, can be co-encapsulated in the nanosized phospholipid vesicles such that a combination composition results. A *cannabis* stock is prepared by adding CBD and/or THC separately or together to the ethanolic stock and mixed at ambient room temperature until completely dissolved. The CBD/THC *cannabis* stock combination is then mixed with a quantity of ethanol, 1:1 to 1:100 (by volume), and further mixed until homogeneous. The ethanol-diluted *cannabis* stock is then combined with a quantity of aqueous solvent, 1:1 to 1:100 (by volume), and mixed until a uniform composition having an opalescent appearance is achieved. The opalescent composition has nanosized spherical phospholipid vesicles that are from 25 nm to 200 nm in diameter. Optionally, the vesicles are sized from 80 nm to 100 nm. Optionally, the vesicles are about 80 nm in diameter.

Optionally, the CBD and THC are combined and encapsulated together in a single addition to the ethanolic stock. Optionally, the CBD and THC are encapsulated separately in the ethanolic stock prior to the addition of the additional ethanol and the vesicles having CBD are combined with the vesicles having THC after addition of the additional ethanol to the individual preparations. Optionally, the CBD and THC encapsulation vesicles are combined prior to the addition of the aqueous solvent. Optionally, the CBD and THC vesicles are combined after addition of the aqueous solvent. The combining of the vesicles with two separately encapsulated materials advantageously allows for tuning of the ratios of the two compounds for specific applications as well as allowing for the maximum concentration of each compound to be individually encapsulated prior to combining.

In another embodiment, the THC is encapsulated as a lipophilic passenger added to the ethanolic stock and mixed with additional ethanol, and water-soluble CBD is added to the aqueous solvent phase, then THC/ethanolic stock/ethanol is combined with the CBD/aqueous solvent to form the final vesicles having both THC and CBD encapsulated therein.

A whole plant *cannabis* stock can be prepared by combining whole plant *cannabis* extracts at a concentration range of 0.1%-10% (w/w) with ethanolic stock and mixed at ambient room temperature until completely dissolved. The whole plant *cannabis* stock is then combined with a quantity of ethanol, 1:1 to 1:100 (by volume) and mixed until homogenous. The ethanol-diluted *cannabis* stock is combined with a quantity of aqueous solvent, 1:1 to 1:100, (by volume) and mixed until a uniform composition having an opalescent appearance is achieved. Optionally, the whole plant extract is a pourable oil, a viscous oil, or a waxy oil. Optionally, the whole plant extract is gently heated to liquefy the oils prior to combining with the ethanolic stock. The opalescent composition has nanosized spherical phospholipid vesicles that are from 25 nm to 200 nm in diameter. Optionally, the vesicles are sized from 80 nm to 100 nm. Optionally, the vesicles are about 80 nm in diameter.

Delivery options comprise encapsulating one or more *cannabis*-derived compounds as passenger molecules in a potentiated nanolipidic process capable of delivering the *cannabis*-derived compound to a subject. Optionally, the route of delivery is oral, via a transmucosal preparation, a sublingual preparation, a buccal preparation, or an oral preparation. Optionally, the delivery route is transdermal via a topically applied preparation, such as a topically applied cream, lotion, ointment, wax, topically applied spray, gel, balm, transdermal patch or other transdermal application means.

*Cannabis sativa*-derived substances which are nanoencapsulated in phospholipid vesicles can be administered in dosages ranging from 1 mg to 300 mg per day in single or divided doses or any dose between 1 mg and 300 mg per day. Optionally, dosages range from 10 mg to 100 mg per day in single or divided doses. Optionally, the dosages range from 1 mg to 20 mg per day in a single or divided dose.

Nanoencapsulated cannabidiol (CBD) for transmucosal delivery is disclosed. The nanoencapsulated lipid vesicles are formulated for transmucosal delivery of the *cannabis*-derived compounds to the mucosa of a subject. Optionally, the mucosa is oral, sublingual or buccal mucosa.

A method of encapsulating *cannabis*-derived compounds for transmucosal delivery is disclosed. The ethanolic stock for preparing the encapsulated nanolipidic preparation is manipulated by dilution with a non-aqueous solvent comprising ethanol and further manipulated by dilution with an aqueous solvent comprising water to achieve the desired transmucosal dose.

Disclosed herein is a formulation for transmucosal delivery of *Cannabis sativa* derived substances in a phospholipid delivery system. The substances can be derived from all varieties of *Cannabis sativa*, including hemp. *Cannabis* varieties used for hemp production are one preferred source of CBD because of a high concentration of CBD with a low concentration of THC in materials from those plants.

Cannabidiol can be extracted from hemp plant materials by a supercritical carbon dioxide extraction process, wherein phase changes induced in the $CO_2$, utilizing temperature and pressure, yield extracts free of toxic solvents. Other organic solvents, such as ethanol, butane, and propane, can also be used to extract *Cannabis*-derived substances, including cannabidiol (CBD), tetrahydrocannabinol (THC), flavonoids and terpenes. The transmucosal preparation is formulated for application to a subject as oral transmucosal, buccal or sublingually-applied liquids (as drops, sprays, aerosols or shots), gels, pastes, lozenges, gums, gummy candies, hard candies, orally dissolving strips, tablets, swish and swallow preparations or other transmucosal application means. Optionally, flavoring or masking agents are added to the preparation prior to administration. The preparation may be applied to the mucosa under the tongue (sublingual), inside the cheeks (buccal), or placed inside the oral cavity. Flavoring or masking agents can be combined with the aqueous solvent used in preparing the phospholipid vesicles.

Disclosed herein is a formulation for transdermal delivery of *Cannabis sativa* derived substances in a phospholipid delivery system. The substances can be derived from all varieties of *Cannabis sativa*, including hemp. *Cannabis* varieties used for hemp production are one preferred source of CBD because of a high concentration of CBD with a low concentration of THC in materials from those plants.

Cannabidiol can be extracted from hemp plant materials by a supercritical carbon dioxide extraction process, wherein phase changes induced in the $CO_2$, utilizing temperature and pressure, yield extracts free of toxic solvents. Other organic solvents, such as ethanol, butane and propane can also be used to extract *Cannabis*-derived substances, including cannabidiol (CBD), tetrahydrocannabinol (THC), flavonoids and terpenes. The transdermal preparation is formulated for application to skin as a cream, lotion, ointment, wax, topically applied spray, gel, balm, transdermal patch or other transdermal application means.

Single cannabinoid isolates, such as CBD and THC, can be encapsulated in nanosized phospholipid vesicles for transmucosal or transdermal delivery to a subject. Preparation of a composition of cannabidiol for transmucosal administration is described.

CBD from the Cannabaceae family, preferably *Cannabis sativa*, can be extracted from the *Cannabis* plant material by a supercritical $CO_2$ extraction process. Cannabidiol (CBD) is procured in a crystalline form having greater than 99% purity. Crystalline CBD useful for encapsulation is a fine white powder having needlelike crystals. While the supercritical $CO_2$ extraction process is preferred, ethanol and butane extractions are also commonly used.

Crystalline CBD having greater than 99% purity is combined with an ethanolic stock having phospholipids and water in an ethanol base until uniformly distributed in the ethanolic stock. Phospholipids used in the ethanolic stock are optionally derived from lecithin. Phospholipids used in the ethanolic stock are optionally derived from soy. When the cannabidiol is fully incorporated into the ethanolic stock, additional ethanol is added to the mixture. A quantity of water is then added to the mixture resulting in discrete nano-sized lipid vesicles having CBD encapsulated in a phospholipid vesicle. Optionally, flavoring or masking agents are combined with the quantity of water before mixing with the cannabidiol-phospholipid mixture.

The CBD concentration in the combined stock ranges from 0.1% to 10%. Optionally, the concentration range is from 1% to 5%. Optionally, the concentration range is from 1.167% to 2.0%. The encapsulated CBD concentration following 1:10 dilution with the aqueous solvent ranges from 0.01% to 1.0%. Optionally, encapsulated CBD concentration following 1:10 dilution with the aqueous solvent ranges from 0.1% to 0.5%. Optionally, the encapsulated CBD concentration following 1:10 dilution with the aqueous solvent ranges from 0.167% to 0.2%.

Table 1 shows a representation of percentages of components in a composition with encapsulated CBD.

TABLE 1

CBD Encapsulation Composition

| Code | Description | INCI | % w/w |
|---|---|---|---|
| A DZ0060 | Ethanolic Stock | Alcohol, Lecithin, Water | 0.833 |
| A CBD (hemp) | Cannabidiol | Cannabidiol | 0.167 |
| B DZ2330 | Ethanol | Alcohol | 9.00 |
| C DZ1370 | Purified Water | Water | 90.00 |
|  |  |  | 100.00 |

Preparations of nanoencapsulated CBD were tested for stability. Results are summarized in Table 2 below.

TABLE 2

Summary of CBD Encapsulation Studies for 1CB

CBD (~99%) Crystalline Stability Studies

| Study Name/Start Date | Vendor of ~99% CBD Crystals | Product Code | *Final CBD Concentration (mg/g) | Day 0 (PSA) | Day 1 (PSA) | Day 2 (PSA) | Day 3 (PSA) | Batch Size | Fill size and Packaging |
|---|---|---|---|---|---|---|---|---|---|
| Study 2 (25° C.) (Jun. 27, 2017) | Isodiol (Lot#ISOB99109) | 1CB | ~1.65 mg/g | (N/A) | (~170 nm) | (N/A) | (~167 nm) | 5 grams of CBD produced and filled into 1 centrifuge tube | 5 g of 1CB in a 15 mL Centrifuge Tube |
| Study 2 (4° C.) (Jun. 27, 2017) |  | 1CB |  | (N/A) | (~185 nm) | (N/A) | (~178 nm) | 5 grams of CBD produced and filled into 1 centrifuge tube |  |
| Study 14B (Jan. 31, 2018) | Isodiol ISO99 (Lot#010918) | 1CB | ~1.65 mg/g | Day 0 Study: 1CB lasted up to 48 hrs Day 7 Study: 1CB lasted up to 24 hrs Day 14 Study: 1CB lasted up to 48 hrs Day 21 Study: 3 bottles of 1CB lasted up to 48 hrs, the other 3 bottles are still in solution 33 Days later Day 35 Study: 1CB lasted up to 48 hrs Day 56 Study: currently in progress | | | | 150 grams of CBD produced and filled into 6 Cobalt Blue Bottles | ~27 g of 1CB in a 1 oz Cobalt Blue Glass Bottle |

TABLE 2-continued

Summary of CBD Encapsulation Studies for 1CB

Combination Material Using a Whole Plant Extract having ~70% Cannabinoids Stability Study

| Study Name/Start Date | Material | Product Code | *Final Concentration of Cannabinoids (mg/g) | Day 0 (PSA) | Day 1 (PSA) | Day 2 (PSA) | Day 3 (PSA) | Batch Size | Fill size and Packaging |
|---|---|---|---|---|---|---|---|---|---|
| Study 6 (Aug. 1, 2017) | **Whole plant Combo Material | 1CB | ~1.17 mg/g | (113.1 nm) | (104.6 nm) | (67.9 nm) | (91.4 nm) | 5 grams produced and filled into 1 centrifuge tube | 5 g of 1CB in a 15 mL Centrifuge Tube |
| Study 6B (Aug. 4, 2017) | **Whole plant Combo Material | 1CB | ~1.17 mg/g | (124.5 nm) | (N/A) | (N/A) | (N/A) | 5 grams produced and filled into 1 centrifuge tube | 5 g of 1CB in a 15 mL Centrifuge Tube |

*Final CBD Concentration dependent on purity of cannabidiol.

Preparations were found to maintain stability from 24 hours up to more than one month.

Example 1: Enhanced Serum Levels of Nano-Encapsulated Vs Non-Encapsulated CBD For transmucosal administration, CBD was encapsulated in a nanosized phospholipid vesicle for the nanoencapsulated preparation, and for comparison purposes, CBD was combined with an olive oil carrier for a non-encapsulated control preparation. The nanoencapsulation vesicles were prepared with a shelf-stable ethanolic stock comprised of water, phospholipids and ethanol, or a similar solvent. Lecithin was used as a source of the phospholipids. The crystalline CBD for use as a control may be dispersed in olive oil, coconut oil or other orally acceptable oil.

Figure 1:
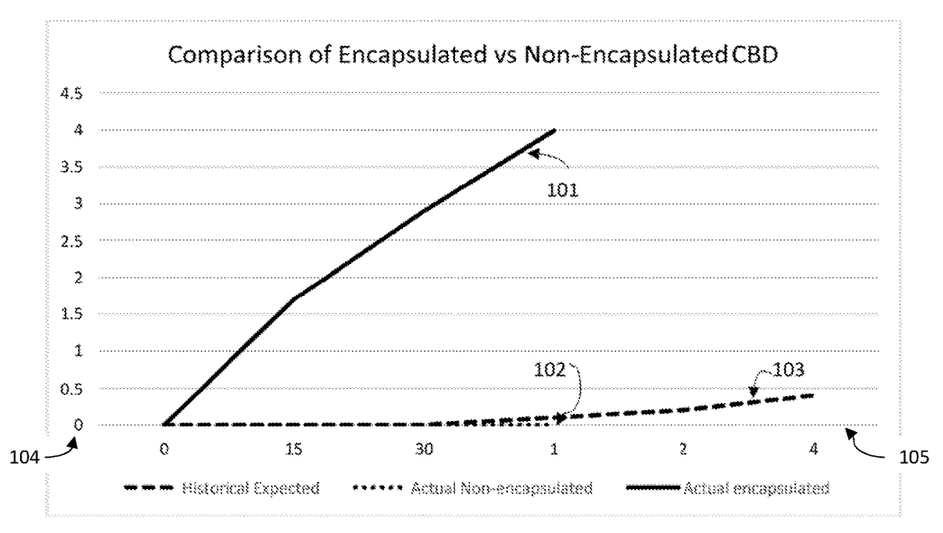
FIG. 1 is a graph showing a comparison of serum levels of encapsulated vs. non-encapsulated CBD against historical data.

Cannabinoids have a greatly increased bioavailability when encapsulated in nanosized phospholipid vesicles as compared to non-encapsulated cannabinoids. FIG. 1 shows a comparison of serum levels achieved for oromucosal administration of cannabidiol encapsulated in nanosized phospholipid vesicles and a control of cannabidiol mixed in olive oil.

In the FIG. 1 graph, a comparison is shown of serum levels in mg/L (104) of encapsulated (101) vs. non-encapsulated (102) CBD against historical data (103) for CBD over time (105). Serum levels from subjects who received transmucosal administration of nano-encapsulated CBD (101) and serum levels from subjects who received transmucosal administration of non-encapsulated CBD in olive oil (102) were compared to historic expected results (103). These historic results for oromucosal bioavailability were compiled from multiple sources for plasma cannabinoid pharmacokinetics.

For the nano-encapsulated and non-encapsulated CBD comparison, test subjects in both groups were administered 1.65 mg CBD, sublingually, and blood samples were collected at regular time intervals and tested for levels of CBD. The FIG. 1 graph shows the serum level results obtained over the first four hours after administration for the nano-encapsulated CBD (101) and the non-encapsulated CBD (102).

For the historic expected results data (103), data was compiled for concentrations of 5, 10 and 15 mg/L and serum levels obtained showed less than one third of the CBD was found in the serum at the peak concentration (C max):

5 mg CBD→1.2 microgram per liter (nanogram per mL) C max;

10 mg CBD→3.0 microgram per liter (nanogram per mL) C max;

15 mg CBD→3.7 microgram per liter (nanogram per mL) C max.

(Tmax=3.6-4.5 hours and AUC (0-10.5 hours=4.1-12.6).

Surprisingly, the serum levels for the nano-encapsulated CBD (101) were not only higher than the historic results would have predicted, they demonstrated a greatly increased bioavailability of the encapsulated CBD over non-encapsulated CBD. The serum yield for a dosing of 1.65 mg CBD→3.99 microgram per liter (nanogram per mL) C 1 hour for the nanoencapsulated CBD. This demonstrates a ten-fold increase in serum concentration of nano-encapsulated CBD over the expected serum concentration of 0.4 microgram per liter as based on historical data for oromucosal bioavailability of CBD.

The serum levels for non-encapsulated CBD were much lower than expected. Based on the historical data, the expectation for non-encapsulated CBD administered in olive oil would be: 1.65 mg CBD→0.4 microgram per liter (nanogram per mL) C max. However, the actual results for non-encapsulated CBD (102) was: 1.65 mg CBD→0.0 microgram per liter (nanogram per mL) C 1 hour indicating that CBD in olive oil was not absorbed.

The invention claimed is:

1. A method of making a combination of nano-encapsulated cannabidiol (CBD) and non-CBD *Cannabis sativa*-derived substances comprising the steps of:
   preparing a first CBD *cannabis* vesicle solution having a first plurality of phospholipid vesicles that contain a nano-encapsulated cannabidiol (CBD), said first *cannabis* CBD solution formed by the steps of:
   providing a cannabidiol (CBD) substance derived from *Cannabis sativa*;
   dissolving said CBD substance in a first quantity of ethanolic solution having 75-89% w/w ethanol, 10-20% w/w phospholipids with phosphatidylcholine (PC) being at least 50% of the phospholipid total, and 1-5% w/w water, to produce a first CBD-ethanolic solution, said ethanolic solution having one or more phospholipid vesicles, said CBD substance having a concentration range in the first CBD-ethanolic solution from 1 part CBD to 10 parts of the first quantity of ethanolic solution up to 10 parts CBD to 1 part of the first quantity of ethanolic solution (w/w);
diluting the first CBD-ethanolic solution with a first quantity of ethanol to produce a first diluted CBD-ethanolic solution, and
mixing the first diluted CBD-ethanolic solution to incorporate the CBD into said first plurality of phospholipid vesicles sized less than 10 nm to produce said first CBD *cannabis* vesicle solution;
preparing a second non-CBD *cannabis* vesicle solution having a second plurality of phospholipid vesicles that contain a nano-encapsulated non-CBD *Cannabis sativa*-derived substance, said second non-CBD *cannabis* solution formed by the steps of:
providing preparing a non-CBD substance derived from *Cannabis sativa*;
dissolving the non-CBD *Cannabis sativa*-derived substance in a second quantity of ethanolic solution having 75-89% w/w ethanol, 10-20% w/w phospholipids with phosphatidylcholine (PC) being at least 50% of the phospholipid total, and 1-5% w/w water, to produce the second non-CBD *cannabis* solution, said ethanolic solution having one or more phospholipid vesicles;
diluting the second non-CBD *cannabis*-ethanolic solution with a second quantity of ethanol to produce a second diluted non-CBD *cannabis*-ethanolic solution, and
mixing the second diluted non-CBD *cannabis*-ethanolic solution to incorporate the non-CBD *Cannabis sativa*-derived substance into said second plurality of phospholipid vesicles sized less than 10 nm to produce said second non-CBD *cannabis* vesicle solution;
combining said first CBD *cannabis* vesicle solution with said second non-CBD *cannabis* vesicle solution to produce a combined *cannabis* vesicle solution;
adding a quantity of water having a pH of 6-8 to the combined *cannabis* vesicle solution; and
mixing said combined *cannabis* vesicle solution with said quantity of water to nano-encapsulate the CBD and non-CBD *Cannabis sativa* derived substances in said combined vesicle solution into phospholipid vesicles sized from 25 nm to 200 nm to produce the combination of nano-encapsulated cannabidiol (CBD) and non-CBD *Cannabis sativa*-derived substances, said concentration of nano-encapsulated CBD in said phospholipid vesicles is from 0.01% to 1.0% w/w.

2. The method of claim 1, wherein the non-CBD *Cannabis sativa*-derived substance is tetrahydrocannabinol (THC), *Cannabis sativa*-derived terpenes, *Cannabis sativa*-derived flavonoids, a whole plant extract of *Cannabis sativa*, or combinations thereof.

3. The method of claim 1, wherein the concentration range of non-CBD *Cannabis sativa* derived substance in the second *cannabis* solution is from 1 part non-CBD *Cannabis sativa*-derived substance to 10 parts of the second quantity of the ethanolic solution up to 10 parts non-CBD *Cannabis sativa*-derived substance to 1 part of the second quantity of the ethanolic solution (w/w).

4. The method of claim 1, wherein the first and second quantities ethanolic solutions have 80% w/w ethanol, 17.75% w/w phospholipids and 2.25% w/w water.

5. The method of claim 1, wherein said quantity of water combined with the combined *cannabis* vesicle solution is at a ratio from 1:5 to 1:25 parts of combined *cannabis* vesicle solution to water (by volume).

6. The method of claim 1, wherein a non-*cannabis* substance is dissolved in the quantity of water prior to combining with the combined *cannabis* vesicle solution.

7. A method of making one or more nano-encapsulated *Cannabis sativa*-derived substances comprising the steps of:
providing a *Cannabis sativa*-derived substance selected from cannabidiol (CBD), tetrahydrocannabinol (THC), *Cannabis sativa*-derived terpenes, *Cannabis sativa*-derived flavonoids, a whole plant extract of *Cannabis sativa*, and combinations thereof;
preparing an ethanolic solution having 75-89% w/w ethanol, 10-20% w/w phospholipids with phosphatidylcholine (PC) being at least 50% of the phospholipid total, and 1-5% w/w water, said ethanolic solution having one or more phospholipid vesicles;
dissolving said *Cannabis sativa*-derived substance in said ethanolic solution to produce a *cannabis* solution; said *Cannabis sativa*-derived substance having a concentration range in the ethanolic solution from 1 part *Cannabis sativa*-derived substance to 10 parts of the ethanolic solution up to 10 parts *Cannabis sativa*-derived substance to 1 part of the ethanolic solution (w/w),
diluting the *cannabis* solution with a quantity of ethanol to produce a first diluted *cannabis* solution;
combining the first diluted *cannabis* solution with a quantity of water having a pH of 6-8 to produce a second diluted *cannabis* solution; and
mixing the second diluted *cannabis* solution to encapsulate the *Cannabis sativa* derived substance in said one or more phospholipid vesicles to produce one or more nano-encapsulated *Cannabis sativa* derived substances, said phospholipid vesicles having a concentration of *Cannabis sativa*-derived substance from 0.01% to 1.0%.

8. The method of claim 7, wherein the *Cannabis sativa*-derived substance is cannabidiol (CBD) or tetrahydrocannabinol (THC).

9. The method of claim 7, wherein the *Cannabis sativa*-derived substance is a combination of cannabidiol (CBD) and tetrahydrocannabinol (THC).

10. The method of claim 7, wherein the ethanolic solution has 80% w/w ethanol, 17.75% w/w phospholipids and 2.25% w/w water.

11. The method of claim 7, wherein phosphatidylcholine (PC) is at least 65% of the phospholipid total in the ethanolic solution.

12. The method of claim 7, wherein the *cannabis* solution has a concentration range of 1 part *Cannabis sativa*-derived substance to to 1 part ethanolic solution (w/w).

13. The method of claim 7, wherein said quantity of ethanol combined with the *cannabis* solution is at a ratio of 1:1 to 1:10 parts of *cannabis* solution to ethanol (by volume).

14. The method of claim 7, wherein said quantity of water combined with the first diluted *cannabis* solution is at a ratio from 1:5 to 1:25 parts of diluted *cannabis* solution to water (by volume).

15. The method of claim 7, wherein the phospholipid vesicles with nano-encapsulated *Cannabis sativa*-derived substance are sized from 25 nm to 200 nm.

16. A method of making one or more nano-encapsulated *Cannabis sativa*-derived substance comprising the steps of:
preparing a *Cannabis sativa*-derived substance;

preparing an ethanolic solution having 75-89% ethanol, 10-20% phospholipids and 1-5% water (w/w) wherein phosphatidylcholine (PC) is at least 50% of the phospholipid total in the ethanolic solution, said ethanolic solution having one or more phospholipid vesicles;

dissolving the *Cannabis sativa*-derived substance in the ethanolic solution to produce a *cannabis* solution;

diluting the *cannabis* solution with a quantity of ethanol to produce a first diluted *cannabis* solution;

combining the diluted *cannabis* solution with a quantity of water having a pH of 6-8 to produce a second diluted *cannabis* solution; and mixing the second diluted *cannabis* solution to encapsulate the *Cannabis sativa* derived substance in said one or more phospholipid vesicle sized from 25 nm to 200 nm to produce one or more nano-encapsulated *Cannabis sativa*-derived substance.

17. The method of claim 16, wherein the *Cannabis sativa*-derived substance is cannabidiol (CBD), tetrahydrocannabinol (THC), *Cannabis sativa*-derived terpenes, *Cannabis sativa*-derived flavonoids, a whole plant extract of *Cannabis sativa*, or combinations thereof.

18. The method of claim 17, wherein the *Cannabis sativa*-derived substance is cannabidiol (CBD) or tetrahydrocannabinol (THC).

19. The method of claim 16, wherein the *cannabis* solution has a concentration range from 1 part *Cannabis sativa*-derived substance to 10 parts ethanolic solution up to 10 parts *Cannabis sativa*-derived substance to 1 part ethanolic solution (w/w).

20. The method of claim 16, wherein a non-*cannabis* substance is dissolved in the quantity of water prior to combining with the diluted *cannabis* solution.

* * * * *